(12) United States Patent
Tanabe

(10) Patent No.: US 9,046,587 B2
(45) Date of Patent: Jun. 2, 2015

(54) SUPERCONDUCTING-MAGNET ADJUSTMENT METHOD

(75) Inventor: Hajime Tanabe, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/360,495

(22) PCT Filed: Mar. 1, 2012

(86) PCT No.: PCT/JP2012/055173
§ 371 (c)(1),
(2), (4) Date: May 23, 2014

(87) PCT Pub. No.: WO2013/128607
PCT Pub. Date: Sep. 6, 2013

(65) Prior Publication Data
US 2014/0329689 A1 Nov. 6, 2014

(51) Int. Cl.
*G01R 33/3873* (2006.01)
*A61B 5/055* (2006.01)
*G01R 33/3815* (2006.01)

(52) U.S. Cl.
CPC ............ *G01R 33/3873* (2013.01); *A61B 5/055* (2013.01); *G01R 33/3815* (2013.01)

(58) Field of Classification Search
CPC .................................................. G01R 33/3873
USPC ............................ 335/216, 301; 324/318–320
See application file for complete search history.

(56) References Cited

U.S. PATENT DOCUMENTS

| | | | |
|---|---|---|---|
| 7,495,441 B2 * | 2/2009 | Amor et al. | 324/318 |
| 8,362,778 B2 * | 1/2013 | Slade | 324/320 |
| 2002/0043975 A1 | 4/2002 | Aoki | |
| 2008/0191698 A1 | 8/2008 | Nogami | |
| 2011/0089943 A1 | 4/2011 | Abe et al. | |

FOREIGN PATENT DOCUMENTS

| | | |
|---|---|---|
| JP | 2002-177243 A | 6/2002 |
| JP | 2003-167941 A | 6/2003 |
| JP | 2008-220923 A | 9/2008 |
| JP | 2008-289703 A | 12/2008 |
| JP | 2011-110065 A | 6/2011 |
| WO | WO 2009/136643 A1 | 11/2009 |

OTHER PUBLICATIONS

International Search Report (PCT/ISA/210) mailed on Apr. 24, 2012, by the Japanese Patent Office as the International Searching Authority for International Application No. PCT/JP2012/055173.

* cited by examiner

*Primary Examiner* — Ramon Barrera
(74) *Attorney, Agent, or Firm* — Buchanan Ingersoll & Rooney PC

(57) ABSTRACT

There are provided the steps of: measuring a magnetic field in a predetermined space; and performing shimming by arranging a plurality of ferromagnetic shims in a superconducting magnet. The step of shimming includes arranging the plurality of shims at positions that make the magnetic field homogeneous, based on a result of measurement in the step of measuring the magnetic field and that provide a predetermined value of an electromagnetic force caused by the magnetic field to act on the plurality of shims.

2 Claims, 10 Drawing Sheets

US 9,046,587 B2

SUPERCONDUCTING-MAGNET ADJUSTMENT METHOD

TECHNICAL FIELD

The present invention relates to a superconducting-magnet adjustment method.

BACKGROUND ART

Japanese Patent Laying-Open No. 2011-110065 (PTD 1) is a prior document disclosing how to assist high-accuracy magnetic-field adjustment for an MRI (Magnetic Resonance Imaging) apparatus.

According to the magnetic-field adjustment method disclosed in PTD 1, a magnetic field generating device has a region to which a target magnetic field distribution is set. An error magnetic field of the magnetic field distribution in this region is reduced to thereby make the magnetic field distribution close to the target magnetic field distribution. A current loop, a ferromagnetic material which is passively magnetized such as an iron piece, or a permanent magnet which does not depend on an external magnetic field is disposed to serve as adjusting means.

Specifically, the magnetic field is adjusted by taking a magnetic field measurement at a predetermined number of points, calculating an error magnetic field that is a difference from a target magnetic field, determining a current potential distribution in a region of a magnetic field adjustment mechanism that can approximately correct the error, converting the current potential distribution into magnetic moments, and arranging a loop current or a magnetic material piece that corresponds to the magnetic moments.

CITATION LIST

Patent Document

PTD 1: Japanese Patent Laying-Open No. 2011-110065

SUMMARY OF INVENTION

Technical Problem

In order to adjust a magnetic field, shimming is performed. An electromagnetic force acting on shims which are used for shimming causes a reaction force to act on a superconducting magnet. Unless shimming is performed in consideration of the electromagnetic force and the reaction force, the magnetic field homogeneity of the superconducting magnet cannot be made stable.

The present invention has been made in view of the above problem, and an object of the present invention is to provide a superconducting-magnet adjustment method that can make the magnetic field homogeneity stable.

Solution to Problem

A superconducting-magnet adjustment method according to the present invention is a method for adjusting homogeneity of a magnetic field generated in a predetermined space by a superconducting magnet. The superconducting-magnet adjustment method includes the steps of: measuring the magnetic field in the predetermined space; and performing shimming by arranging a plurality of ferromagnetic shims in the superconducting magnet. The step of shimming includes arranging the plurality of shims at positions that make the magnetic field homogeneous, based on a result of measurement in the step of measuring the magnetic field and that provide a predetermined value of an electromagnetic force caused by the magnetic field to act on the plurality of shims.

Advantageous Effects of Invention

In accordance with the present invention, the magnetic field homogeneity can be made stable.

DESCRIPTION OF EMBODIMENTS

Figure 1:
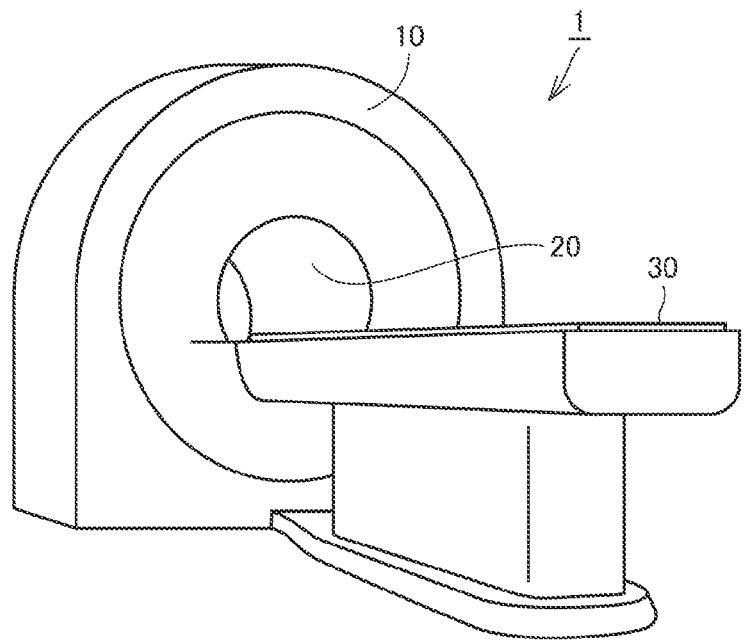
FIG. 1 is a perspective view showing an external appearance of an MRI apparatus.

The following describes a method for adjusting a superconducting magnet in a first embodiment of the present invention, with reference to the drawings. In the description below of embodiments, the same or corresponding portions are given the same reference characters and are not described repeatedly.

While the following description of the embodiments is made in connection with a superconducting magnet for MRI, the superconducting magnet is not limited to this but may be the one used for other purposes. In addition, while the superconducting magnet to be described below is cylindrical, the superconducting magnet is not necessarily limited to the cylindrical superconducting magnet, and the present invention is also applicable to an open-type superconducting magnet.

First Embodiment

FIG. 1 is a perspective view showing an external appearance of an MRI apparatus. As shown in FIG. 1, MRI apparatus 1 includes a static magnetic field generating unit 10 and a bed 30. Static magnetic field generating unit 10 includes a superconducting magnet described later herein, and generates a static magnetic field in a bore 20.

Figure 2:
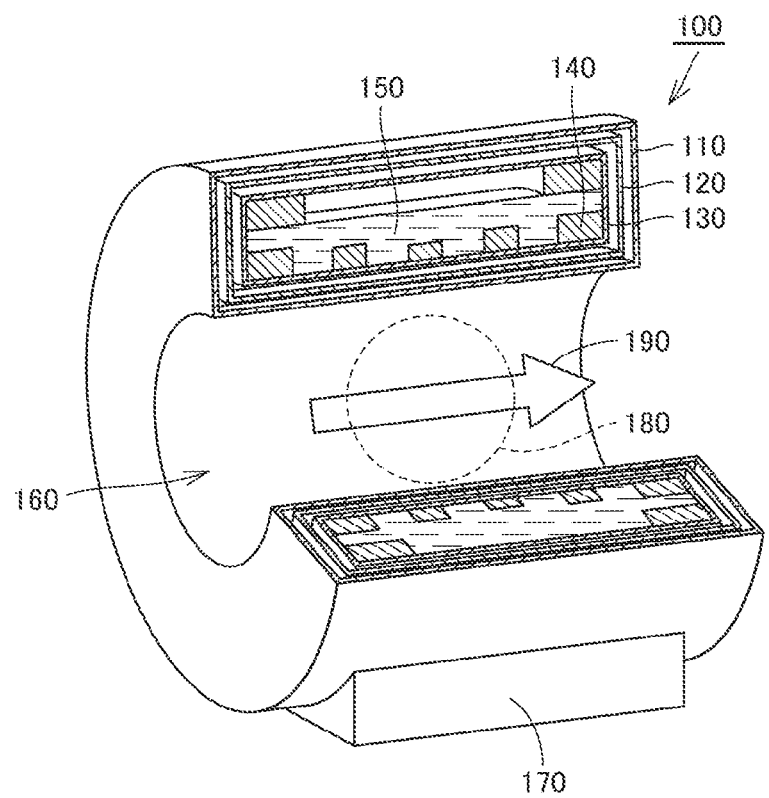
FIG. 2 is a cross sectional view showing a structure of a superconducting magnet in a first embodiment of the present invention.

FIG. 2 is a cross sectional view showing a structure of the superconducting magnet in the first embodiment of the present invention. As shown in FIG. 2, a vacuum cell 110 having a hollow cylindrical shape is disposed at the outermost side in superconducting magnet 100 in the first embodiment of the present invention. A central space of the cylindrical vacuum cell 110 serves as a bore portion 160 corresponding to bore 20. The pressure within vacuum cell 110 is reduced by a decompression device (not shown) to generate a vacuum therein. Vacuum cell 110 is supported by a leg 170 disposed below vacuum cell 110, so as to allow the central axis of bore portion 160 to extend in the horizontal direction.

In vacuum cell 110, a heat shield 120 is disposed which has a hollow cylindrical shape substantially similar to that of vacuum cell 110. In heat shield 120, a helium cell 130 is disposed which has a hollow cylindrical shape substantially similar to that of heat shield 120. Heat shield 120 has a function of providing thermal insulation between helium cell 130 and vacuum cell 110.

In helium cell 130, superconducting coils 140 are disposed circumferentially. Helium cell 130 is filled with liquid helium 150. Superconducting coils 140 are immersed and cooled in liquid helium 150.

When superconducting magnet 100 becomes operational, a static magnetic field 190 is generated in the direction of an arrow, which is shown in the drawing, in a static magnetic field region 180 indicated by a dotted line in bore portion 160. It is desired that this static magnetic field 190 is strong, homogeneous, and stable.

Figure 3:
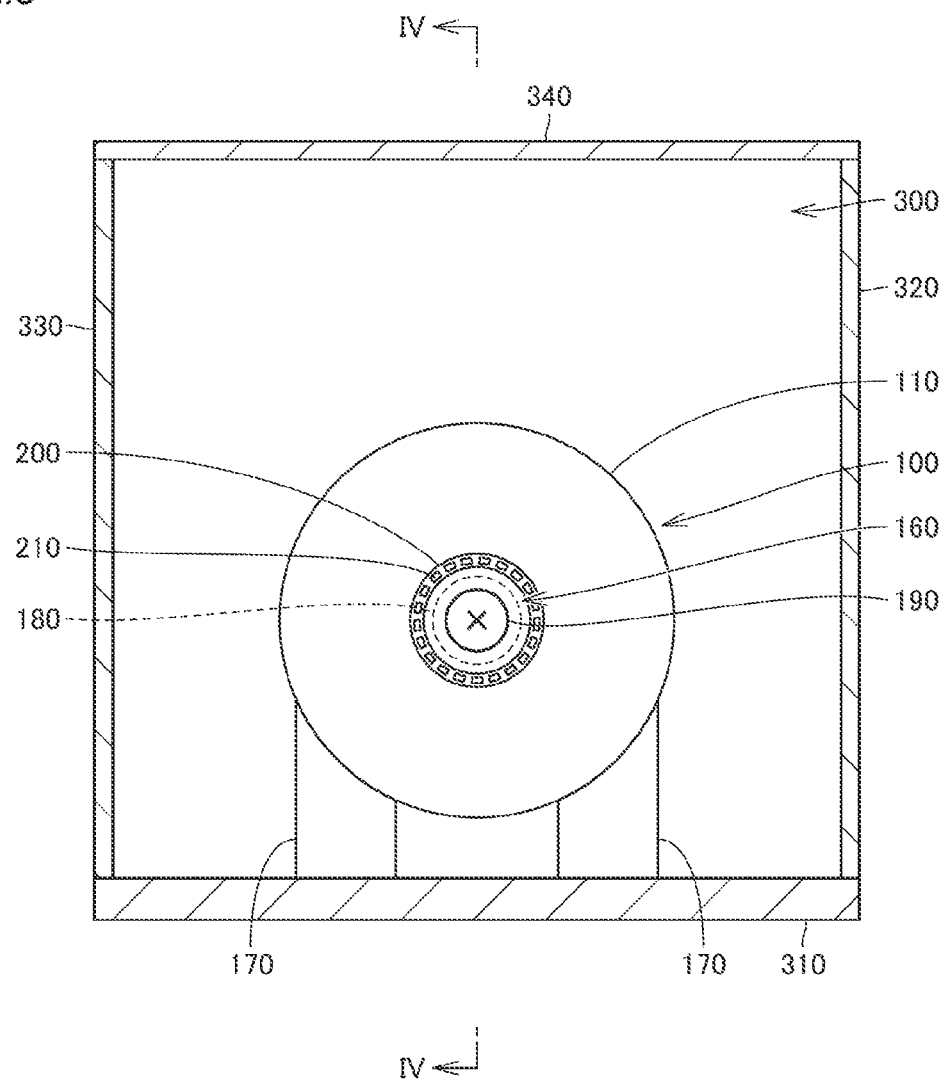
FIG. 3 is a side view of the superconducting magnet of the embodiment installed in a place for use.
Figure 4:
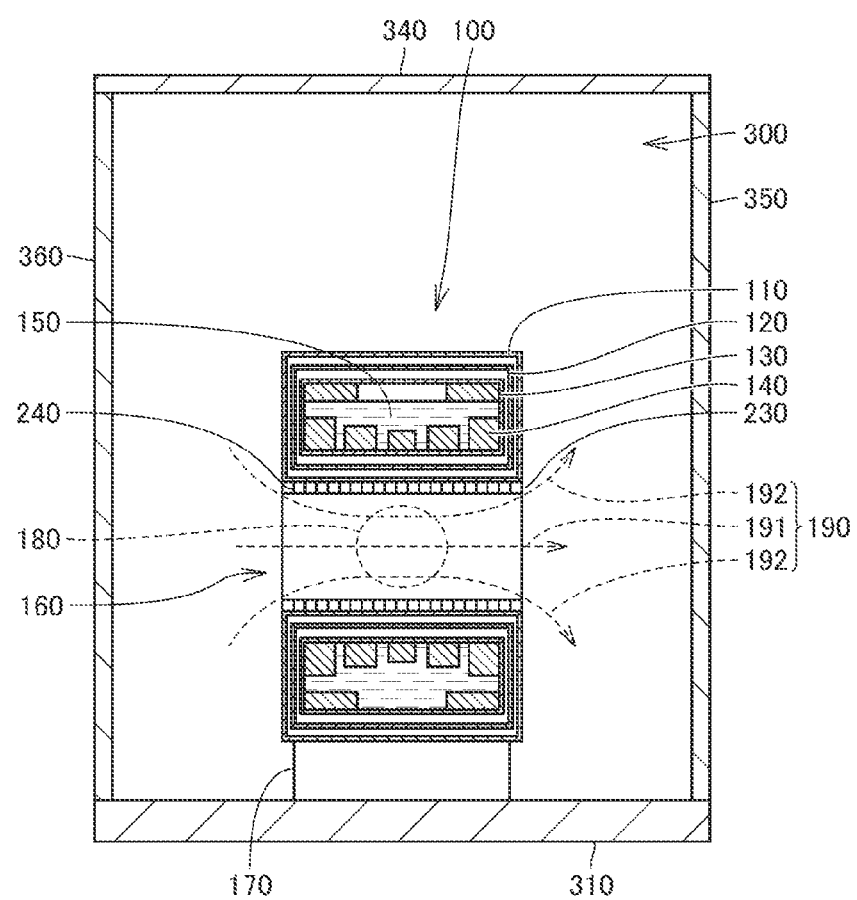
FIG. 4 is a diagram as seen in the direction of arrows of line Iv-Iv in FIG. 3.

FIG. 3 is a side view of the superconducting magnet of the present embodiment installed in a place for use. FIG. 4 is a diagram as seen in the direction of arrows of line IV-IV in FIG. 3.

As shown in FIGS. 3 and 4, superconducting magnet 100 of the present embodiment is installed in a room 300, which is a place for use. In the present embodiment, room 300 is covered with magnetic shields so that leakage, from room 300, of a strong magnetic field generated by superconducting magnet 100 is reduced.

The magnetic shields include: a floor shield 310 disposed along the floor; a first sidewall shield 320 disposed along a sidewall portion on the right side of FIG. 3; a second sidewall shield 330 disposed along a sidewall portion on the left side of FIG. 3; a third sidewall shield 350 disposed along a sidewall portion on the right side of FIG. 4; a fourth sidewall shield 360 disposed along a sidewall portion on the left side of FIG. 4; and a ceiling shield 340 along the ceiling. In the present embodiment, each of the magnetic shields is formed of an iron plate. The material for the magnetic shield, however, is not particularly limited as long as it is made of a magnetic material.

Because floor shield 310 is located relatively close to superconducting magnet 100 and bears the weight of superconducting magnet 100, floor shield 310 is formed thicker than first sidewall shield 320, second sidewall shield 330, third sidewall shield 350, fourth sidewall shield 360, and ceiling shield 340.

As shown in FIG. 4, static magnetic field 190, which is illustrated in a simplified manner in FIG. 2, includes a central magnetic field 191 generated on the central axis of bore portion 160, and edge-side magnetic fields 192 generated at the radial edge portions of bore portion 160. Each of edge-side magnetic fields 192 is generated in the form of a straight line in static magnetic field region 180, and is generated in the form of a curve at each of the edge portions of bore portion 160 in the central axis direction thereof.

Figure 5:
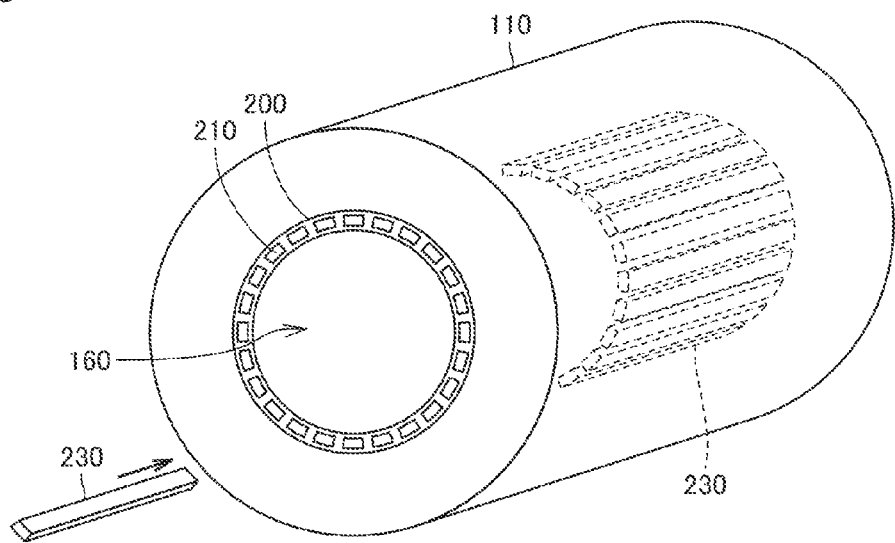
FIG. 5 is a perspective view showing a shimming portion in the superconducting magnet of the embodiment.
Figure 6:
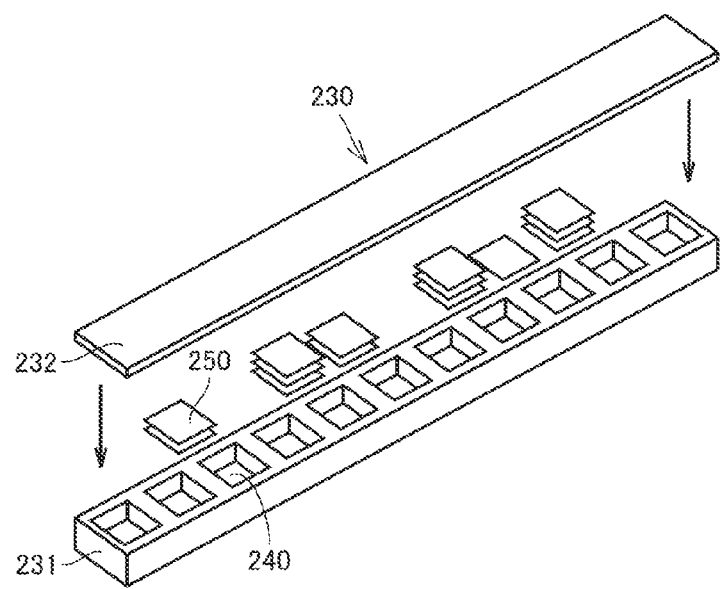
FIG. 6 is an exploded perspective view showing a shim tray and iron pieces in the embodiment.

FIG. 5 is a perspective view showing a shimming portion in the superconducting magnet of the present embodiment. FIG. 6 is an exploded perspective view showing a shim tray and iron pieces in the present embodiment.

As shown in FIGS. 3 and 5, superconducting magnet 100 has a shimming portion 200 formed to extend along the inner circumferential sidewall of vacuum cell 110, which, however, is not shown in FIG. 2. In shimming portion 200, a plurality of openings 210 are provided with spaces therebetween in the circumferential direction of shimming portion 200, and extend in the central axis direction of bore portion 160.

As shown in FIGS. 4, 5, and 6, a shim tray 230 is inserted into each of openings 210. As shown in FIG. 6, shim tray 230 includes a main body 231 and a cover 232. Main body 231 is provided with recesses 240 for accommodating therein a plurality of iron pieces 250 each formed of a rectangular thin plate. In the present embodiment, iron piece 250 is used as a shim. The shim, however, is not limited to this but may be a ferromagnetic plate or block.

Adjustment can be made to the number of iron pieces 250 accommodated in each of a plurality of recesses 240 of a plurality of shim trays 230 to be inserted into openings 210 respectively, to thereby improve the homogeneity of static magnetic field 190 in static magnetic field region 180. As such, shimming is performed to improve the homogeneity of static magnetic field 190 in static magnetic field region 180 by disposing iron pieces 250 in this way.

Figure 7:
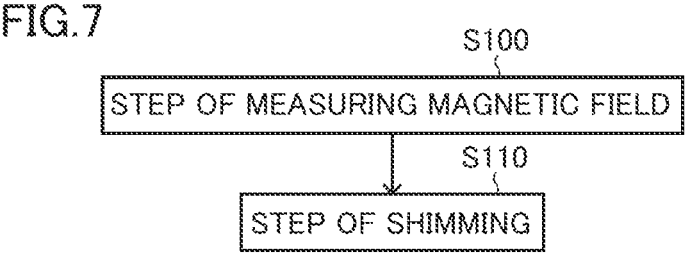
FIG. 7 is a flowchart of a superconducting-magnet adjustment method in the embodiment.

FIG. 7 is a flowchart of a superconducting-magnet adjustment method in the present embodiment. As shown in FIG. 7, the superconducting-magnet adjustment method in the present embodiment includes: firstly measuring a magnetic field in static magnetic field region 180 (S100); and then performing shimming by arranging iron pieces 250 in superconducting magnet 100 (S110).

Figure 8:
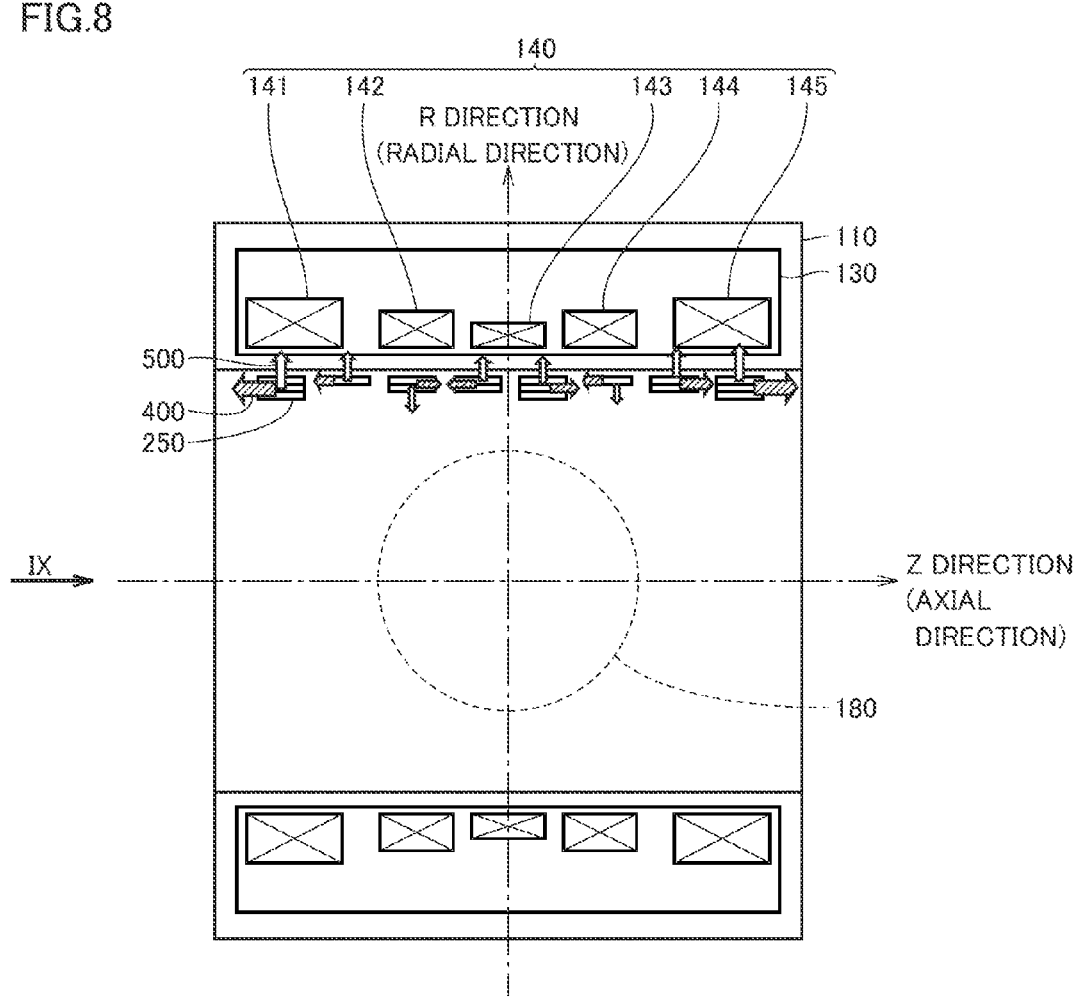
FIG. 8 is a cross-sectional view showing a plurality of iron pieces arranged in the superconducting magnet in the embodiment.
Figure 9:
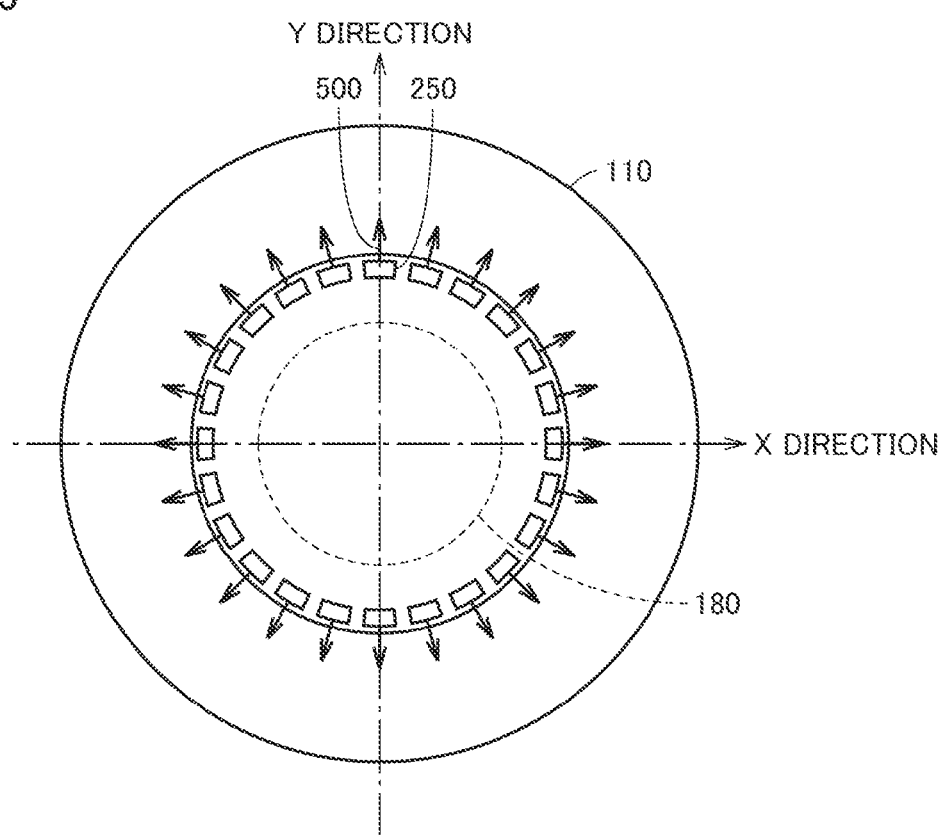
FIG. 9 is a side view of the superconducting magnet of FIG. 8 as seen in the direction of an arrow of line IX.

FIG. 8 is a cross-sectional view showing a plurality of iron pieces arranged in the superconducting magnet in the present embodiment. FIG. 9 is a side view of the superconducting magnet of FIG. 8 as seen in the direction of an arrow of line IX. FIG. 8 shows only those iron pieces arranged in the top portion of shimming portion 200, among a plurality of iron pieces. In addition, among the constituent parts of shimming portion 200, only iron pieces 250 are shown.

As shown in FIGS. 8 and 9, an electromagnetic force caused by the static magnetic field generated by superconducting magnet 100 acts on each of a plurality of iron pieces 250. Generally, among superconducting coils 140, endmost superconducting coils 141, 145 are largest, their adjacent superconducting coils 142, 144 are second largest, and centrally-located superconducting coil 143 is smallest in size, as shown in FIG. 8. Accordingly, magnetic forces generated respectively around these superconducting coils differ in magnitude from each other.

The electromagnetic force acting on each of a plurality of iron pieces 250 varies in direction and numerical value, depending on the position where a plurality of iron pieces 250 are each arranged. The direction and the numerical value of the electromagnetic force vary non-linearly between iron pieces adjacent in the axial direction from each other. As shown in FIGS. 8 and 9, on each of a plurality of iron pieces 250, an electromagnetic force 400 acts in the axial direction (Z direction) of superconducting magnet 100 and an electromagnetic force 500 acts in the radial direction (R direction) of superconducting magnet 100. Electromagnetic force 500 acting in the radial direction (R direction) consists of a component in the horizontal direction (X direction) and a component in the vertical direction (Y direction) shown in FIG. 9.

The conventional superconducting-magnet adjustment method determines the positions of iron pieces 250 that make the magnetic field in static magnetic field region 180 homogeneous, based on the result of calculation through simulation provided by dedicated software. Specifically, a simulative calculation is made to determine positions of iron pieces 250, among a plurality of positions where a plurality of iron pieces 250 can be arranged, that can provide the most homogeneous magnetic field.

In the case of such simulation, commonly there are a plurality of patterns of arrangement of iron pieces 250 that can provide the most homogeneous magnetic field. In the present embodiment, a pattern of arrangement that provides a predetermined value of the electromagnetic force acting on a plurality of iron pieces 250 is selected from these patterns.

Figure 10:
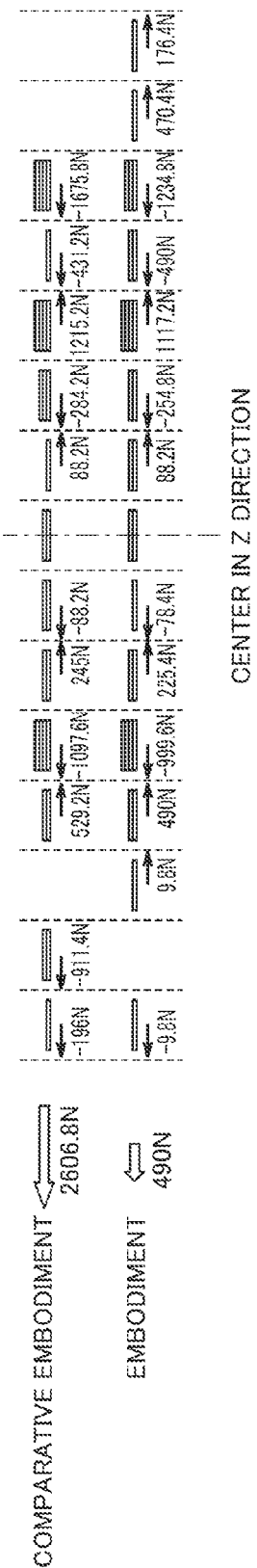
FIG. 10 is a diagram showing an electromagnetic force acting on iron pieces in a comparative embodiment that are arranged in consideration of only the magnetic field homogeneity, and an electromagnetic force acting on iron pieces in the embodiment that are arranged in consideration of both the magnetic field homogeneity and the electromagnetic force.

FIG. 10 is a diagram showing an electromagnetic force acting on iron pieces in a comparative embodiment that are arranged in consideration of only the magnetic field homogeneity, and an electromagnetic force acting on iron pieces in the present embodiment that are arranged in consideration of both the magnetic field homogeneity and the electromagnetic force.

In FIG. 10, an electromagnetic force acting in the leftward direction as seen in FIG. 10 is indicated by a negative value, and an electromagnetic force acting in the rightward direction as seen therein is indicated by a positive value. FIG. 10 shows only those iron pieces arranged in the top portion of shimming portion 200, among a plurality of iron pieces.

As shown in FIG. 10, a plurality of iron pieces 250 are arranged for example in 15 columns in the axial direction (Z direction) of superconducting magnet 100. In this case, the position of the eighth column is the central position in the Z direction. Both the arrangement of iron pieces in the comparative embodiment and that in the present embodiment can provide a homogeneous magnetic field in static magnetic field region 180.

In the present embodiment, iron pieces 250 are arranged at positions that can make a largest reduction of the electromagnetic force acting, in the axial direction of superconducting magnet 100, on a plurality of iron pieces 250. Namely, the method for adjusting superconducting magnet 100 in the present embodiment arranges, in the step of shimming (S110), a plurality of iron pieces 250 at positions that provide the most homogeneous magnetic field in static magnetic field region 180 based on the result of measurement of the step of measuring a magnetic field (S100) and that make a largest reduction of an electromagnetic force caused by the magnetic field to act on a plurality of iron pieces 250.

As shown in FIG. 10, the absolute value of the total electromagnetic force acting on a plurality of iron pieces 250 is 2606.8 N in the comparative embodiment, while it is 490 N in the present embodiment.

Figure 11:
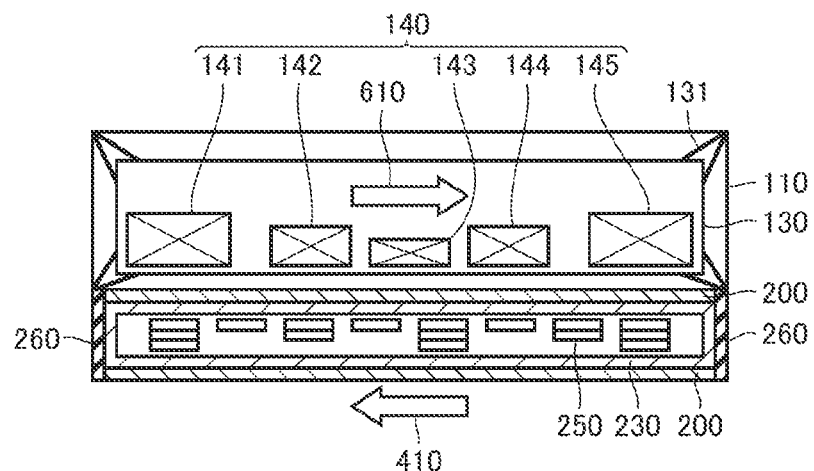
FIG. 11 is a partial cross-sectional view schematically showing an electromagnetic force acting on a plurality of iron pieces in the embodiment.

FIG. 11 is a partial cross-sectional view schematically showing an electromagnetic force acting on a plurality of iron pieces in the present embodiment. FIG. 11 shows only the top portion of shimming portion 200. In FIG. 11, heat shield 120 is not shown.

As shown in FIG. 11, an electromagnetic force 410 acting on a plurality of iron pieces 250 is accompanied by its reaction force 610 acting on superconducting coils 140. Electromagnetic force 410 and reaction force 610 each have the total value as shown in FIG. 10. Reaction force 610 acting on superconducting coils 140 is exerted on a support member 131 which supports helium cell 130.

Support member 131 couples helium cell 130 and vacuum cell 110 to each other. For support member 131, a material of low thermal conductivity and high strength is used. For example, GFRP (Glass Fiber Reinforced Plastic) is used for support member 131. Support member 131 contacts only the corner and its vicinity of helium cell 130, so that the area where support member 131 and helium cell 130 contact each other is small.

In the case where large electromagnetic force 410 acts on iron pieces 250 as in the above-described comparative embodiment, the resultant reaction force 610 is also large, which may cause deformation of support member 131 with time. In this case, helium cell 130 may be positionally displaced to thereby narrow the thermal insulation space between helium cell 130 and vacuum cell 110. Accordingly, the temperature in helium cell 130 may increase or condensation may occur in vacuum cell 110. In this case, cooling of superconducting coil 140 may become unstable to thereby deteriorate the magnetic field homogeneity in static magnetic field region 180.

As in the present embodiment, reduction of the electromagnetic force acting on iron pieces 250 and the resultant reduction of reaction force 610 can suppress deformation of support member 131 and thereby make cooling of superconducting coils 140 stable with time. Accordingly, the magnetic field homogeneity in static magnetic field region 180 can be made stable.

Meanwhile, electromagnetic force 410 acting on a plurality of iron pieces 250 is exerted on an anti-vibration rubber 260 positioning shim tray 230 which accommodates a plurality of iron pieces 250. In the present embodiment, anti-vibration rubbers 260 are provided respectively on the two opposite ends in the axial direction of superconducting magnet 100. Namely, anti-vibration rubbers 260 located on the opposite ends of shimming portion 200 serve as lids.

In the case where a large electromagnetic force acts on iron pieces 250 as in the above-described comparative embodiment, a high load is exerted on anti-vibration rubber 260, which may cause anti-vibration rubber 260 to deform with time. In this case, shim tray 230 may be positionally displaced to change the positions of a plurality of iron pieces 250 in the tray and thereby cause deterioration of the magnetic field homogeneity in static magnetic field region 180.

As in the present embodiment, reduction of the electromagnetic force acting on iron pieces 250 can suppress deformation of anti-vibration rubber 260 and thereby make the positions of a plurality of iron pieces 250 stable with time. Accordingly, the magnetic field homogeneity in static magnetic field region 180 can be made stable.

While the present embodiment arranges a plurality of iron pieces 250 so that the electromagnetic force acting in the axial direction (Z direction) of superconducting magnet 100 is reduced. Alternatively, a plurality of iron pieces 250 may be arranged so that the electromagnetic force acting in the radial direction (R direction) is reduced.

The following describes a superconducting-magnet adjustment method in a second embodiment of the present invention. The superconducting-magnet adjustment method in the present embodiment differs from that of the first embodiment only in terms of a predetermined value of the electromagnetic force which is to act on a plurality of iron pieces 250. Therefore, the description of other features is not repeated.

Second Embodiment

Figure 12:
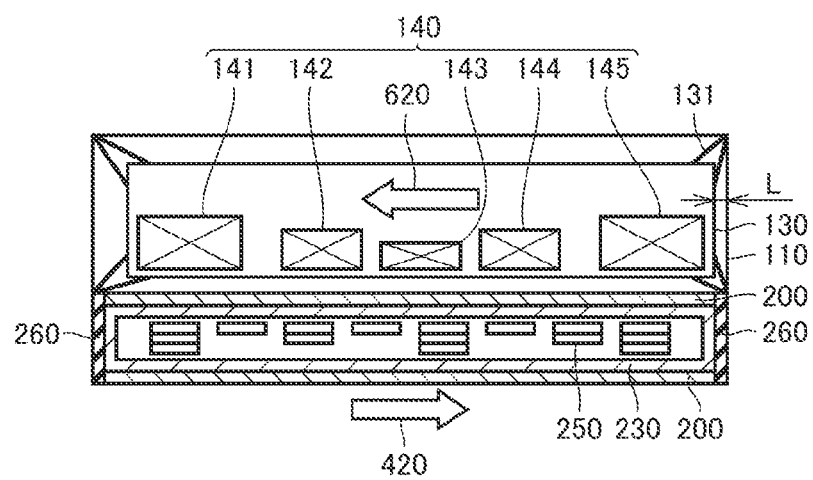
FIG. 12 is a partial cross-sectional view schematically showing an electromagnetic force acting on a plurality of iron pieces in a second embodiment of the present invention.

FIG. 12 is a partial cross-sectional view schematically showing an electromagnetic force acting on a plurality of iron pieces in the second embodiment of the present invention. FIG. 12 shows only the top portion of shimming portion 200. In FIG. 12, heat shield 120 is not shown.

As shown in FIG. 12, the direction of the electromagnetic force acting on a plurality of iron pieces 250 in the present embodiment is made opposite, with respect to the axial direction of superconducting magnet 100, to the direction thereof in the first embodiment. While FIG. 12 shows iron pieces 250 located similarly to FIG. 11, iron pieces 250 are actually arranged at positions different from those shown in FIG. 11.

When parts have been assembled into superconducting magnet 100, a distance L between helium cell 130 and vacuum cell 110 may be shorter than a set value for example, due to accumulation of dimensional errors of the parts and assembly errors. In this case, the thermal insulation space between helium cell 130 and vacuum cell 110 may be narrowed to cause an increase of the temperature in helium cell 130 or occurrence of condensation in vacuum cell 110 as described above.

In view of this, the present embodiment arranges a plurality of iron pieces 250 so that a reaction force 620 resultant from an electromagnetic force 420 acting on a plurality of iron pieces 250 is exerted on helium cell 130. Accordingly, distance L between helium cell 130 and vacuum cell 110 can be increased. Electromagnetic force 420 and reaction force 620 each have the total value as shown in FIG. 10.

In this way, the positional displacement of helium cell 130 caused during assembly into superconducting magnet 100 can be improved. This is applicable not only to the positional displacement of helium cell 130 but also to the positional displacement of other constituent parts.

It should be noted that if an increase of electromagnetic force 420 for the purpose of increasing reaction force 620 is excessively large, anti-vibration rubber 260 is deformed. Therefore, in consideration of this, the predetermined value of electromagnetic force 420 has to be set to a certain value.

Figure 13:
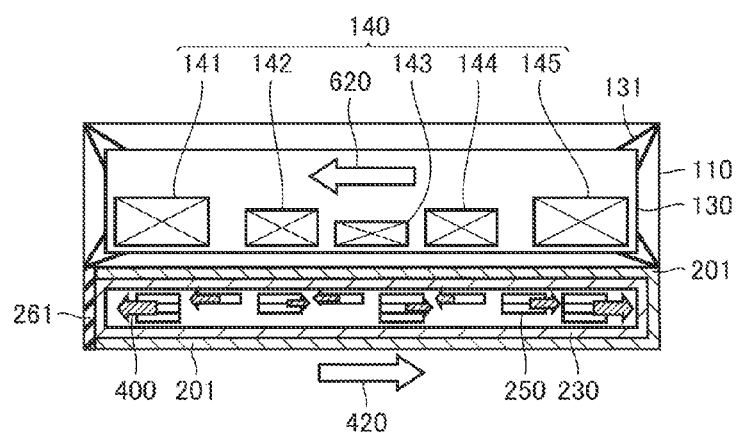
FIG. 13 is a partial cross-sectional view schematically showing an electromagnetic force acting on a plurality of iron pieces in a modification of the embodiment.

FIG. 13 is a partial cross-sectional view schematically showing an electromagnetic force acting on a plurality of iron pieces in a modification of the present embodiment. FIG. 13 shows only the top portion of a shimming portion 201. In FIG. 13, heat shield 120 is not shown.

As shown in FIG. 13, shimming portion 201 in the modification of the present embodiment has one end in the axial direction of superconducting magnet 100 that is a closed end. Shimming portion 201 has the other end in the axial direction of superconducting magnet 100 that is provided with an anti-vibration rubber 261.

Shim tray 230 accommodating a plurality of iron pieces 250 can be placed to contact the closed end of shimming portion 201 to thereby position a plurality of iron pieces 250 in the axial direction of superconducting magnet 100.

In view of the above, the modification of the present embodiment provides electromagnetic force 420 having a predetermined value and acting, toward the aforementioned closed end, on a plurality of iron pieces 250, to thereby cause shim tray 230 to contact the closed end of shimming portion 201.

In this way, a load can be prevented from being exerted on anti-vibration rubber 261 while the positional accuracy of a plurality of iron pieces 250 is improved. Accordingly, the magnetic field homogeneity in static magnetic field region 180 can be made stable.

The direction of electromagnetic force 420 and that of reaction force 620 are not limited to the above-described ones. For example, respective directions of electromagnetic force 420 and reaction force 620 may be adjusted so that a load is exerted on a member having resistance to a compressive stress or a member having its shape stabilized by receiving a predetermined stress.

The following describes a superconducting-magnet adjustment method in a third embodiment of the present invention. The superconducting-magnet adjustment method in the present embodiment differs from that of the second embodiment only in that the electromagnetic force acting in the radial direction of superconducting magnet 100 is set to a predetermined value. Therefore, the description of other features is not repeated.

Third Embodiment

Figure 14:
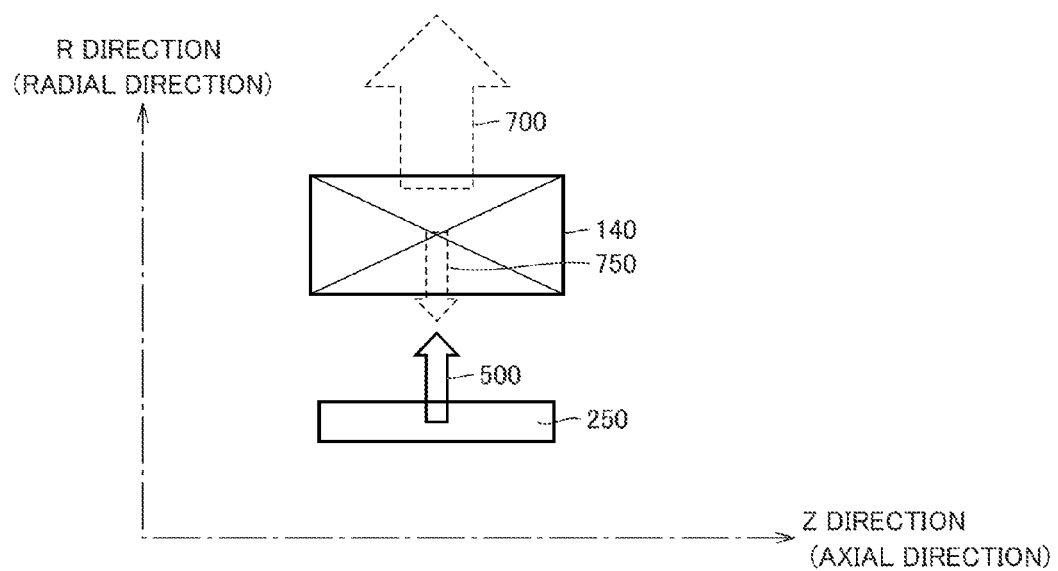
FIG. 14 is a partial cross-sectional view schematically showing an electromagnetic force acting on a plurality of iron pieces in a third embodiment of the present invention.

FIG. 14 is a partial cross-sectional view schematically showing an electromagnetic force acting on a plurality of iron pieces in the third embodiment of the present invention. FIG. 14 exemplarily shows one of a plurality of superconducting coils 140 and one of a plurality of iron pieces 250.

In the condition that iron pieces 250 are not attached, an expansive force (hoop force) 700 in the radially outward direction acts on superconducting coil 140. When disturbance of more than an allowable amount occurs to superconducting magnet 100 due to the influence of expansive force 700, a quench, which is a phenomenon of breaking the superconducting state, occurs.

In the present embodiment, as shown in FIG. 14, a plurality of iron pieces 250 are arranged so that a reaction force 750 resultant from an electromagnetic force 500 acting, in the radial direction of superconducting magnet 100, on a plurality of iron pieces 250 is exerted on superconducting coils 140. Electromagnetic force 500 and reaction force 750 each have the total value as shown in FIG. 10.

The direction of reaction force 750 is opposite to that of expansive force 700. Therefore, reaction force 750 and expansive force 700 are superimposed on and cancel each other. Thus, expansive force 700 is reduced, a quench is made less likely to occur, and cooling of superconducting coil 140 can be made stable with time. Accordingly, the magnetic field homogeneity in static magnetic field region 180 can be made stable.

It should be construed that the embodiments disclosed herein are given by way of illustration in all respects, not by way of limitation. The technical scope of the present invention is defined based on claims, rather than interpreted based on the embodiments only, and encompasses all modifications and variations equivalent in meaning and scope to the claims.

REFERENCE SIGNS LIST

1 MRI apparatus; 10 static magnetic field generating unit; 20 bore; 30 bed; 100 superconducting magnet; 110 vacuum cell; 120 heat shield; 130 helium cell; 131 support member; 140, 141, 142, 143, 144, 145 superconducting coil; 150 liquid helium; 160 bore portion; 170 leg; 180 static magnetic field region; 190 static magnetic field; 191 central magnetic field; 192 edge-side magnetic field; 200, 201 shimming portion; 210 opening; 230 shim tray; 231 main body; 232 cover; 240 recess; 250 iron piece; 260, 261 anti-vibration rubber; 300 room; 310 floor shield; 320 first sidewall shield; 330 second sidewall shield; 340 ceiling shield; 350 third sidewall shield; 360 fourth sidewall shield; 400, 410, 420, 500 electromagnetic force; 610, 620, 750 reaction force; 700 expansive force

The invention claimed is:

1. A superconducting-magnet adjustment method for adjusting homogeneity of a magnetic field generated in a predetermined space by a superconducting magnet including a superconducting coil, comprising the steps of:

measuring the magnetic field in said predetermined space; and performing shimming by arranging a plurality of shims of a ferromagnetic material in the superconducting magnet, said step of shimming including arranging said plurality of shims at positions that make the magnetic field homogeneous, based on a result of measurement in said step of measuring the magnetic field and that provide an electromagnetic force generating a reaction force which acts, in a radially inward direction of the superconducting magnet, on said superconducting coil so that said reaction force cancels and reduces an expansive force which acts in a radially outward direction on the superconducting coil in a condition where said shims are not attached.

2. The superconducting-magnet adjustment method according to claim 1, wherein said step of shimming uses iron shims as said shims.

* * * * *